United States Patent

Ishii et al.

[11] Patent Number: 6,089,101
[45] Date of Patent: Jul. 18, 2000

[54] MATERIAL TESTING MACHINE INCLUDING A CONTROL SYSTEM FOR FEEDBACK-CONTROLLING THE OPERATION OF A SERVO SYSTEM

[75] Inventors: Yuzo Ishii; Nobunari Takahashi, both of Toyohashi; Tatsuyoshi Kotou, Kitakyushu, all of Japan

[73] Assignee: Japan Tobacco Inc., Tokyo, Japan

[21] Appl. No.: 09/132,897

[22] Filed: Aug. 12, 1998

[30] Foreign Application Priority Data

Aug. 13, 1997 [JP] Japan .................................. 9-218551
Aug. 13, 1997 [JP] Japan .................................. 9-218552

[51] Int. Cl.$^7$ ...................................................... G01N 3/00
[52] U.S. Cl. .............................................................. 73/798
[58] Field of Search ............................. 73/788, 790, 796, 73/798, 804, 807

[56] References Cited

U.S. PATENT DOCUMENTS

| | | |
|---|---|---|
| 4,003,246 | 1/1977 | Cain . |
| 4,096,741 | 6/1978 | Sternstein ................................. 73/817 |
| 4,235,114 | 11/1980 | Mohler .................................... 73/805 |
| 4,567,466 | 1/1986 | Bozarth et al. . |
| 5,092,179 | 3/1992 | Ferguson .................................. 73/790 |

FOREIGN PATENT DOCUMENTS 3248033  11/1991  Japan .

OTHER PUBLICATIONS

Patent Abstracts of Japan, JP 03 248033 A, Nov. 6, 1991, vol. 016, No. 042.

Patent Abstracts of Japan, JP 09 203700 A, Aug. 5, 1997, vol. 1997, No. 12.

Database WPI, XP002123691, Feb. 7, 1993, Section EI, Week 199413, Derwent Publications Ltd., SU 1 793 428.

*Primary Examiner*—Max Noori
*Attorney, Agent, or Firm*—Birch, Stewart, Kolasch & Birch, LLP

[57] ABSTRACT

A material testing machine includes a control system for feedback-controlling, during material testing, the operation of a servo system including an actuator for applying a load to a test piece. During the mounting of the test piece to the testing machine, a target displacement of a movable part of the actuator is corrected in accordance with the actual load applied to the test piece so as to prevent the actual load from being excessive. While the amplification factor of an amplifier for detecting the controlled variable is being changed over during the material testing, a control output value supplied from a digital controller of the control system to the servo system is maintained at a value obtained just before the changeover of the amplification factor, whereby the detection scale factor in detecting the controlled variable can be maintained at a constant value.

5 Claims, 7 Drawing Sheets

MATERIAL TESTING MACHINE INCLUDING A CONTROL SYSTEM FOR FEEDBACK-CONTROLLING THE OPERATION OF A SERVO SYSTEM

BACKGROUND OF THE INVENTION

1. Technical Field

The present invention relates to a material testing machine, and more particularly, to an electrohydraulic servo-controlled material testing machine.

2. Related Art

An electrohydraulic servo-controlled material testing machine is known which is comprised of a controller for supplying, via a servo amplifier, an electric signal input to an electrohydraulic servo valve provided between a hydraulic power source and a hydraulic actuator such as a hydraulic cylinder, the electric signal input varying in accordance with a target displacement of a movable part of the actuator. Typically, the quantity of fluid output from the servo valve varies in response to the electric signal input, and the movable part of the hydraulic cylinder is displaced at a speed proportional to the fluid quantity, whereby a load is applied to a test piece held between the cylinder movable part and a main body of the testing machine. An actual displacement of the cylinder movable part is detected and is supplied as a feedback signal to the controller. Under the control of the controller, a feedback control is carried out to cause the actual displacement to be close to a target displacement.

In this specification, the term "displacement of a test piece" indicates the displacement of one end of the test piece coupled to a movable part of an actuator which is caused by the displacement of the movable part of the actuator. In a material testing machine of a type provided with two actuators having movable parts which hold a test piece therebetween and are typically displaced in opposite directions, the term "displacement of the test piece" indicates the sum of displacements of opposite ends of the test piece caused by the displacement of the two movable parts of the actuators. That is, the term "displacement of the test piece" indicates deformation of the test piece caused by the displacement of the movable part(s) of the actuator.

The term "servo system" indicates a system mainly comprised of an actuator, a servo amplifier, and a servo valve. The term "control system" indicates a system mainly comprised of a servo system and a controller for controlling the operation of the servo system. The term "control loop" or "feedback control loop" indicates a loop mainly comprised of a servo system, a controller, and a test piece. Moreover, the term "force control system" indicates a control system for carrying out a feedback control with use of an actual force applied to the test piece, as the controlled variable, whereas the term "displacement control system" indicates a system for executing a feedback control using, as a controlled variable, an actual displacement of the test piece. The term "load" indicates a broadly defined load which includes a force applied to the test piece and generally referred to as a load, and which also includes the displacement of the test piece. If the actual load or the actual displacement is referred to as a controlled variable, the term "control objective value" or "control target value" indicates a target load.

In order to detect the controlled variable (the actual force applied to or the actual displacement of the test piece) in the feedback control performed in the testing machine, a detection amplifier which is mainly comprised of a highly sensitive analog amplifier is employed. The detection signal, indicative of the controlled variable and supplied from an analog detection system including such a detection amplifier, is liable to be affected by external disturbance such as electric power noise, especially when the controlled variable is small in magnitude, i.e., when the level of the detection signal is low. Thus, it is difficult to attain a sufficient signal-to-noise ratio, causing the control accuracy to be lowered.

In order to ensure an adequate signal-to-noise ratio (SN ratio), a multi-range detection amplifier may be employed which has plural ranges such as a ×1 range, ×2 range, ×5 range, and ×10 range and which permits range-selection to select a desired range, whereby the amplification factor (amplification gain) is changeable in dependence on the level of the detection signal. Further, as proposed in Japanese provisional patent publication no. 3-248033, the level of the control objective value (target load) is sometimes adjusted in synchronism with the range selection. Moreover, in order to eliminate turbulence in the control caused by a deviation between the timing of range selection and that of level adjustment for the control objective value, the arrangement disclosed in this patent publication is provided with a hold circuit which holds an error between the control objective value and the detected value obtained just before the range selection. However, the loop gain in the entirety of the feedback control system changes upon range selection for changing the amplification factor of the detection amplifier. To compensate for a change in the loop gain caused by the range selection, the feedback control system, including a controller configured by a digital circuit, requires reestablishment of the control gain when the range selection is made. Therefore, a large scale control must be made, if the control objective value is changed in synchronism with the range selection as proposed in the aforementioned patent publication. In addition, the range selection in the detection amplifier comprised of an analog amplifier generally requires much time in the order of several tens of milliseconds, whereas the level adjustment for the control objective value in the digital control system can be rapidly made within a time period in the order of 100 microseconds. Unstable operation of the digital control system can be found due to a large deviation between the completion timing at which the level adjustment in the digital control system is finished and the completion timing of the range selection in the analog detection system.

Prior to material testing, it is desired to stably mount a test piece onto the body of a testing machine. Especially, it is preferable to prevent the test piece from receiving an excessive load during the mounting work and from receiving an undesired load on and after completion of the mounting work. However, it is difficult for the operator to stably mount the test piece onto the machine body under his or her visual observations.

Heretofore, If that the test piece is mounted between stationary and movable chucks of the machine body, a first end portion of the test piece is mounted to the movable chuck coupled to the movable part of the hydraulic actuator of the machine, and then the hydraulic actuator is manually operated to cause a second end portion of the test piece to gradually move toward the stationary chuck in a condition that the actual force applied to the test piece is monitored by a load meter. When a slight actual force applied to the test piece is detected, it is determined that the test piece is brought in light contact with the stationary chuck, and then the second end portion of the test piece is grasped by the stationary chuck. However, the force generated when the test piece is brought in contact with the stationary chuck greatly varies depending on the stiffness of the test piece, and an excessive force may be applied to the test piece even if the displacement of the movable part of the hydraulic actuator is small in magnitude. In addition, the test piece mounted to the machine body is already applied with a force at that time. Thus, it is difficult to establish the initial state where the test piece is at no load.

SUMMARY OF THE INVENTION

An object of the present invention is to provide a material testing machine capable of stably performing range selection in an analog detection system for detecting actual load, without the need of adjusting the control gain in a digital controller which constitutes a control system of the testing machine.

Another object of the present invention is to provide a material testing machine capable of stably easily mounting a test piece to the machine body under non-load conditions, without applying excessive load to the test piece.

According to one aspect of the present invention, there is provided a material testing machine for measuring a mechanical property of a test piece based on a load given to the test piece and a mechanical change (e.g., displacement or distortion) generated in the test piece, while feedback-controlling an operation of a servo system including a hydraulic actuator which gives the load to the test piece by means of a controller such that actual load applied to the test piece coincides with a target load.

The material testing machine comprises: a detection amplifier for detecting a load applied to the test piece or a mechanical change generated in the test piece and for outputting an analog detection value, the detection amplifier being operable at an amplification factor selected from a plurality of amplification factors; range selection means for switching the amplification factor of the detection amplifier; detection scale-factor invariant means for processing a digital detection value, converted from the analog detection value supplied from the detection amplifier, in dependence on the selected amplification factor of the detection amplifier, to thereby cause a detection scale factor in detecting a controlled variable in the feedback control to be invariant; and control output holding means for holding a control output value at a value observed just before the amplification factor is switched, while the amplification factor of the detection amplifier is being switched, the control output value being supplied to the servo system from a digital controller which performs a feedback-control action in accordance with the processed digital detection value.

Preferably, the detection scale-factor invariant means includes an analog-to-digital converter for converting the analog output value supplied from the detection amplifier into the digital detection value, and a digital coefficient unit for performing coefficient processing in which the digital detection value supplied from the analog-to-digital converter is processed in accordance with the selected amplification factor of the detection amplifier such that the detection scale factor is rendered invariant.

Preferably, the control output holding means is comprised of a hold circuit for holding an output value supplied from the digital coefficient unit just before the amplification factor of the detection amplifier is switched, until the switching of the amplification factor is completed.

With this testing machine or its preferred arrangements, the detection scale factor in detecting the controlled variable given to the digital controller (e.g., a force applied to or a mechanical change generated in the test piece) can be kept unchanged even if the amplification factor of the detection amplifier is switched by the range selection. This eliminates the need of adjusting the control output value supplied from the digital controller or the control gain for the digital controller in synchronism with the range selection, whereby the control system can be simplified in construction. In addition, a control error caused by a deviation between the timing at which the range selection is made in the analog detection system and the timing at which the level adjustment of the control output value is made in the digital controller can be absorbed, whereby the range selection can be stably carried out and the operation of the digital control system can be stabilized. This makes it easy to handle the testing machine and improve the testing efficiency.

According to another aspect of the present invention, the material testing machine comprises: a machine body having a test piece mount which is coupled to a movable part of the actuator; a displacement control system including a controller for feedback-controlling the operation of the servo system so as to cause an actual displacement of the movable part of the actuator to coincide with a target displacement; a force detector for detecting an actual force applied to the test piece as the movable part of the actuator is displaced; and correction means for correcting the target displacement of the movable part of the actuator in accordance with the actual force applied to the test piece such that the actual force does not exceed a predetermined force, as the test piece is mounted to the machine body while executing the feedback control by the displacement control system.

With this testing machine, during the mounting of the test piece to the machine body while controlling the displacement of the actuator movable part by means of the displacement control system, the target displacement per se of the actuator movable part is corrected such that the actual force applied to the test piece does not exceed a predetermined force. This makes it possible to accurately specify the displacement position of the actuator movable part, without causing an abrupt change in target displacement, whereby the test piece can be mounted to the testing machine body in a stable manner. Thus, the test piece mounting work can be made easier and efficiently.

Preferably, the correction means corrects the target displacement so as to decrease when the actual force, applied to the test piece and detected by the force detector, exceeds a detection resolution of the force detector.

With this preferred arrangement, if a slight actual force is detected during the test piece mounting to the machine body, the target displacement is corrected to decrease, and hence the actual force applied to the test piece can be reduced to substantially zero. This makes it possible to mount the test piece to the machine body under non-load conditions.

These and other features and advantages will be apparent from a detailed description of particular embodiments of this invention illustrated as non-exclusive examples in the appended drawings.

DETAILED DESCRIPTION

With reference to the appended drawings, an electrohydraulic servo-controlled material testing machine according to an embodiment of the present invention will be explained.

Figure 1:
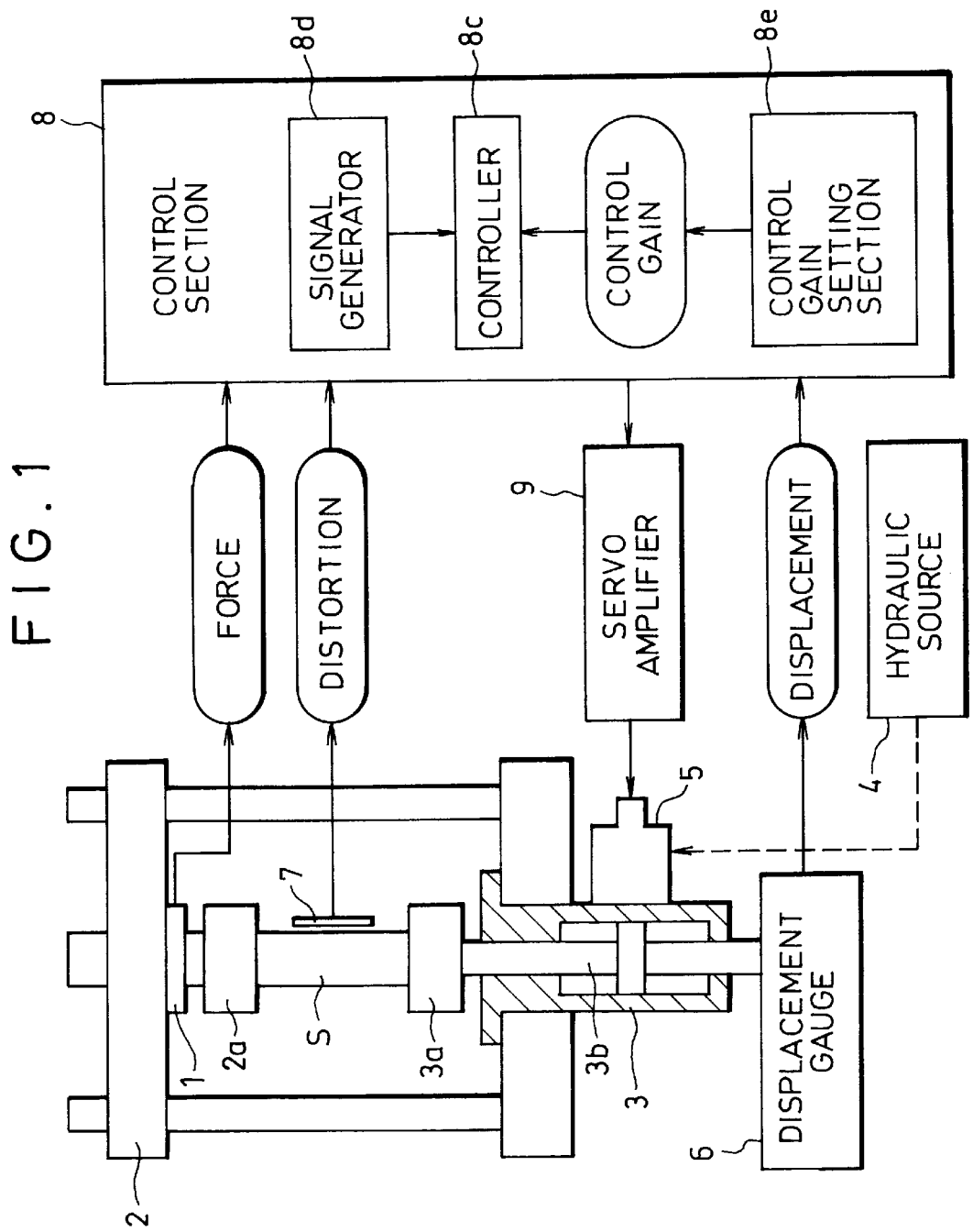
FIG. 1 is a schematic view showing the basic construction of a material testing machine according to an embodiment of the present invention.

As shown in FIG. 1, the testing machine is so configured as to supply a pressurized fluid (fluid pressure) from a hydraulic source 4 to an actuator 3, comprised of a hydraulic cylinder, through a servo valve 5 to operate a movable rod 3b of the actuator 3, thereby providing a load to a test piece S which is held between a stationary chuck 2a provided on the side of a frame of a machine body and a movable chuck 3a provided on the actuator-side. Depending on the type of material testing, the stationary chuck 2a may be removed and a die may be provided instead of the movable chuck 3a, so as to attach the test piece S between the die 3a and a load cell 1.

An actual force applied to the test piece S from the movable rod 3b is detected by the load cell 1, displacement of the test piece S is detected by a displacement gauge 6, and distortion of the test piece S is detected by a distortion gauge 7 attached to the test piece. A controller 8c of a control section 8 which is comprised of a microcomputer and the like inputs the detected force, displacement and distortion, and controls the operation of the servo valve 5 via a servo amplifier 9 in a feedback manner, with use of a control gain which is set by a control gain setting section 8e, so as to reduce an error between the force detected by the load cell 1 and a target force given from a signal generator 8d of the control section 8 to zero. The hydraulic actuator 3 is servo-controlled by the servo feedback control system to adjust a force (more generally, load) applied to the test piece S.

Figure 2:
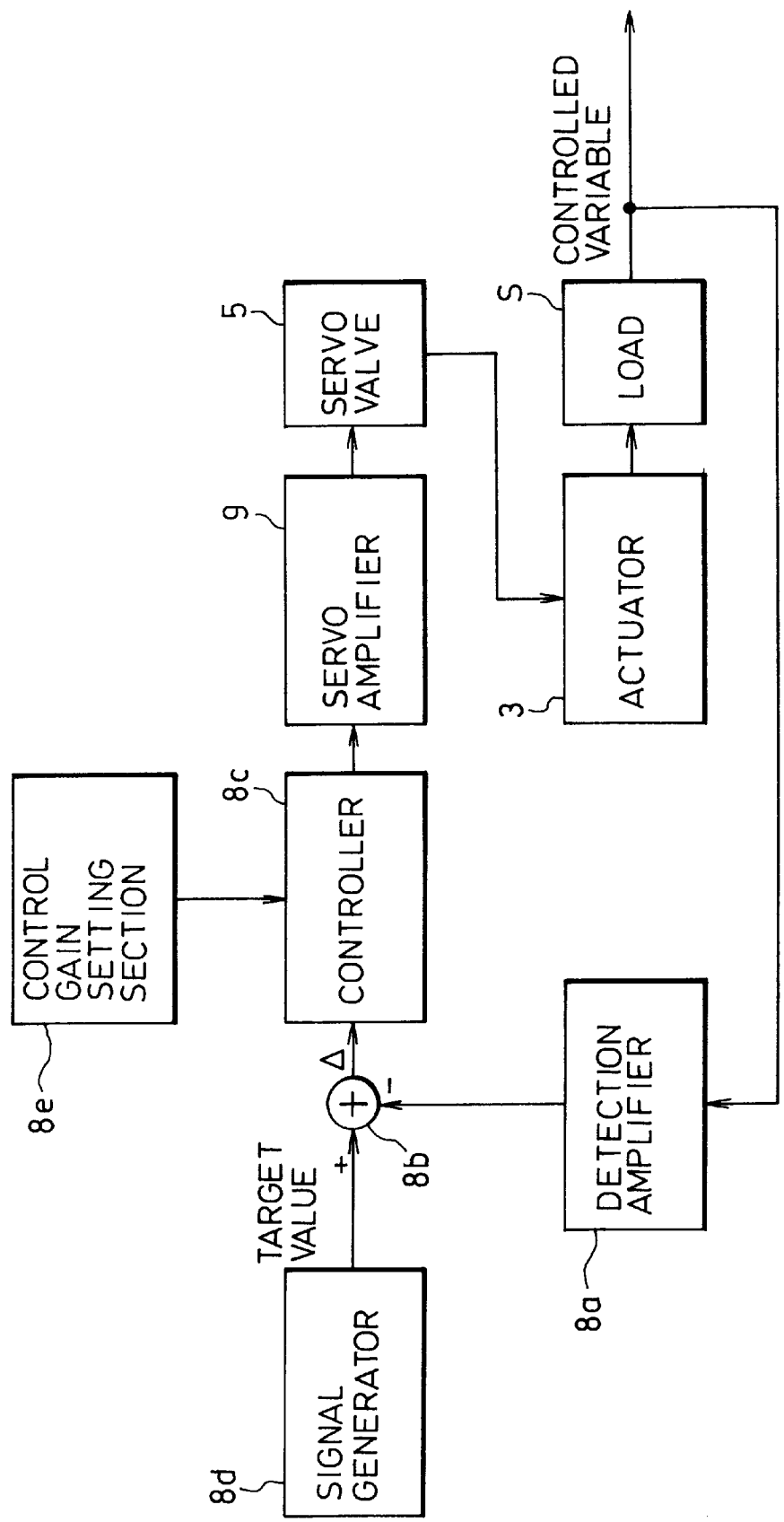
FIG. 2 is a block diagram showing a control loop in the testing machine shown in FIG. 1.

The electrohydraulic servo control system is represented by a feedback control loop, as shown in FIG. 2. More specifically, the control system comprises an error unit 8b for determining an error Δ between a control objective value (a target load or a target displacement, for example) and an output of a detection amplifier 8a which indicates a change (an actual force or an actual displacement) generated in the test piece S, and a controller 8c for controlling, via a servo amplifier 9, the operation of the servo valve 5 in accordance with the error determined by the error unit 8b. Thus, the control system controls the operation of the servo valve 5 so as to reduce the error Δ to zero, thereby hydraulically driving the actuator 3 to adjust the load applied to the test piece S.

Figure 3:
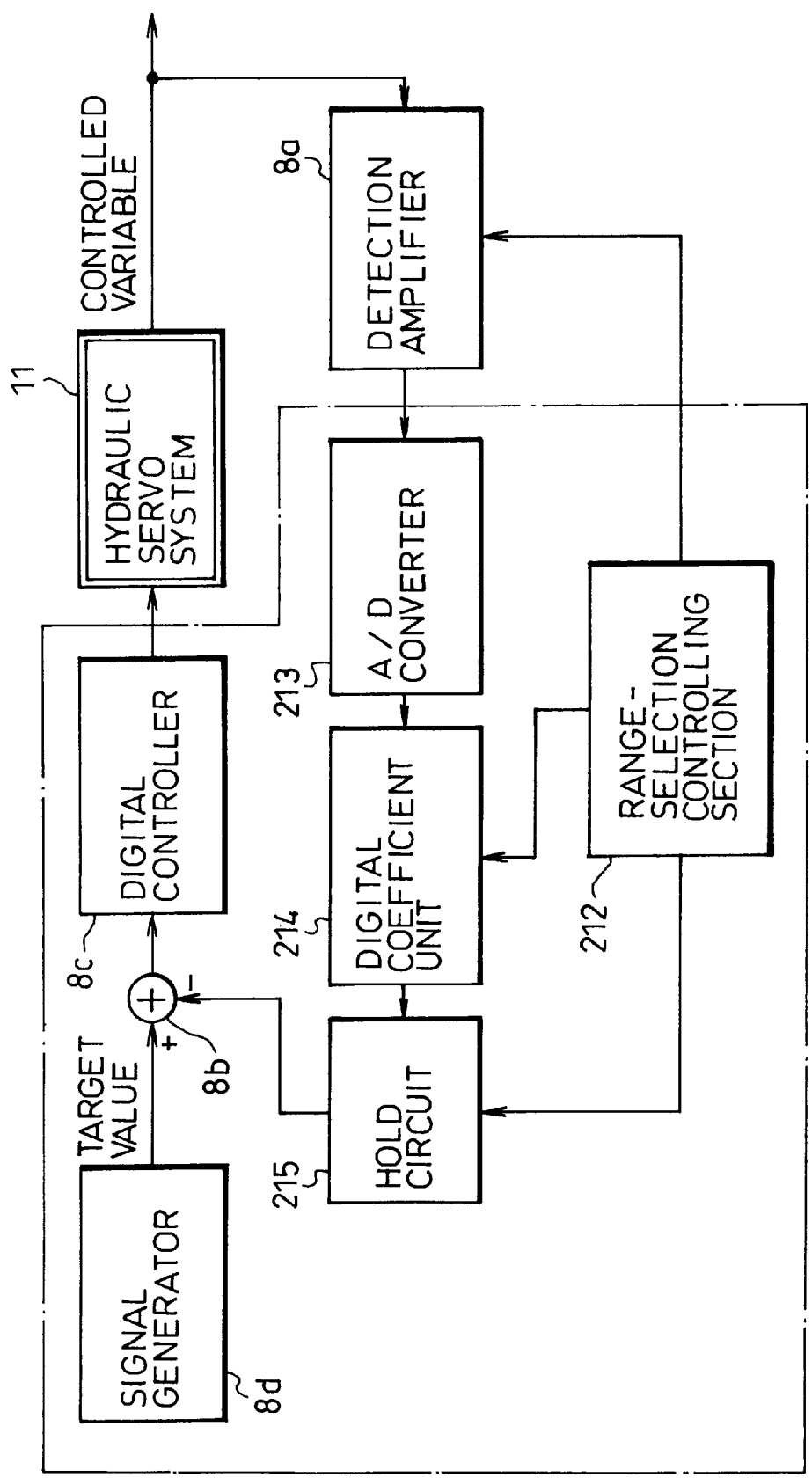
FIG. 3 is a block diagram showing a range selecting function of the control system of the material testing machine.

A first feature of the testing machine resides in that, as shown in FIG. 3, the testing machine comprises an analog detection system mainly comprised of a detection amplifier 8a and a digital control system which is mainly comprised of the digital controller 8c. The digital control system is configured to carry out a digital feedback control in which the operation of the servo system 11 is digitally controlled in accordance with the detection value detected through the detection amplifier 8a and indicative of the force applied to the test piece S or the displacement generated in the test piece. Further, the digital control system is configured to subject the detection value of force or displacement to an analog-to-digital conversion and reads the resultant digital detection value, and digitally calculates the control output for the servo system 11, with use of a predetermined control gain, in accordance with the error Δ between the digital detection value and the control target value given by the signal generator 8d. The digital control system serves as a PI or PID control system.

The detection amplifier 8a is operable at an arbitrary one of, e.g., four amplification factors such as ×1, ×2, ×5 and ×10.

The digital control system comprises a range-selection controlling section 212 for selecting and setting the amplification factor of the detection amplifier 8a, an AD converter 213 for subjecting the detection value, supplied from the detection amplifier 8a and regarding the force or displacement, to an analog-to-digital conversion to thereby obtain a digital detection value, a digital coefficient unit 214 for coefficient-processing the digital detection value in accordance with the range (amplification factor) set in the detection amplifier 8a, and a hold circuit 215 for holding the coefficient-processed digital detection value. The error unit 8b determines the error between the coefficient-processed digital detection value supplied from the hold circuit 215 and the control target value generated by the signal generator 8d. The digital controller 8c controls the operation of the servo system 11 in accordance with the error and with use of a predetermined control gain. The operations of the digital coefficient unit 214 and the hold circuit 215 are controlled by the range-selection controlling section 212.

In the following, characteristic functions and operations of the control system as constructed above will be explained.

The detection amplifier 8a which is comprised of a highly sensitive analog amplifier is arranged such that the amplification factor of the amplifier 8a is selectively set under the control of the range-selector controlling section 212. The range selection of the detection amplifier 8a is carried out on a hardware-basis, e.g., by changing a circuit constant of the amplifier. A time period in the order of several tens of milliseconds is required to change the circuit constant.

On the contrary, various functional sections of the control section 8 such as the AD converter 213 and the digital coefficient unit 214 are configured to execute the operational processing at intervals of a control cycle, e.g., 100 μsec. Further, the coefficient employed in the coefficient processing in the digital coefficient unit 214 is also switched and set within the control cycle. Under the control of the range-selection controlling section 212 and in synchronism with the range selection in the detection amplifier 8a, the coefficient in the digital coefficient unit 214 is switched to have a value which is inversely proportional to the amplification factor in the detection amplifier 8a, whereby the product of the amplifier factor in the detection amplifier 8a and the coefficient value in the digital coefficient unit 214, i.e., the detection scale factor in detecting the force applied to the test piece S or the displacement of the test piece, is kept unchanged. For instance, if the amplification factor in the detection amplifier 8a is set to ×10, the coefficient value in the digital coefficient unit 214 is modified to a value which is one-tenth of an ordinary coefficient value which is used when the amplification factor is set to ×1, whereby the output of the AD converter 213 is converted into one-tenth, thereby maintaining the detection scale factor unchanged.

More specifically, if the force detected by the load cell 1 is in the order of one-tenth of a maximum force, the amplification factor in the detection amplifier 8a is set to, e.g., ×10, in order to detect the force highly sensitive with an adequate signal-to-noise ratio (hereinafter referred to as SN ratio). In this case, the level of a signal indicative of the controlled variable and supplied from the detection amplifier 8a is ten times larger than the ordinary signal level. The digital coefficient unit 214 carries out the coefficient processing in respect of the digital detection value, obtained through the AD converter 213 in which the output signal of the detection amplifier 8a is subjected to an analog-to-digital conversion, with use of a coefficient value which is inversely proportional to the amplification factor of the detection amplifier 8a, thereby achieving a function of restoring the level of the controlled variable supplied to the error unit 8b to an ordinary level.

The detection scale factor is kept at a constant by means of the coefficient processing effected in synchronism with the range selection for the detection amplifier 8a, so that the noise component such as electric power noise affecting the analog detection system is reduced, thereby improving the SN ratio. As a consequence, an erroneous action in the control system attributable to noise is prevented, and the operation of the control system is stabilized. That is, if the amplification factor of the detection amplifier 8a is increased, the force or displacement is detected with high sensitivity, with the level of the noise component affecting the detection system kept at a constant. As a consequence, the ratio of the noise component level to the detection signal level can be reduced.

The operation mode changeover in the digital control system upon range selection in the detection amplifier 8a is carried out at a timing determined by the control cycle and at a high speed. For this reason, if the range selection is instructed during the feedback control for the servo system 11, a deviation will inevitably occurs between the mode changeover timing in the digital control system and the range selection timing in the detection amplifier 8a. In this respect, the range-selection controlling section 212 causes the hold circuit 215 to operate in such a manner that the control output supplied from the digital controller 8c to the servo system 11 is maintained at a constant until the range selection in the detection amplifier 8a is completed.

More specifically, when the range-selection instructing signal is automatically supplied from the control program or is supplied manually by the operator, the range-selection controlling section 212 gives range selection instructions to the detection amplifier 8a and the digital coefficient unit 214, and at the same time gives the instructions to the hold circuit 215 to hold the output of the digital coefficient unit 214 for a certain period of time. Until this time period has elapsed from the time at which the range-selection instructions are given, the detection value just before the range selection is instructed is supplied to the error unit 8b. On and after the range selection is completed in the detection amplifier 8a, the detection value is accurately determined through the digital coefficient unit 214 in which the mode changeover or coefficient value changeover was already completed. Thus, after elapse of the prescribed time period from when the range selection was instructed, the range-selection controlling section 212 gives instructions to the hold circuit 215 to release the action of holding the digital detection value, so that the output of the digital coefficient unit 214 is supplied to the error unit 8b.

Figure 4:
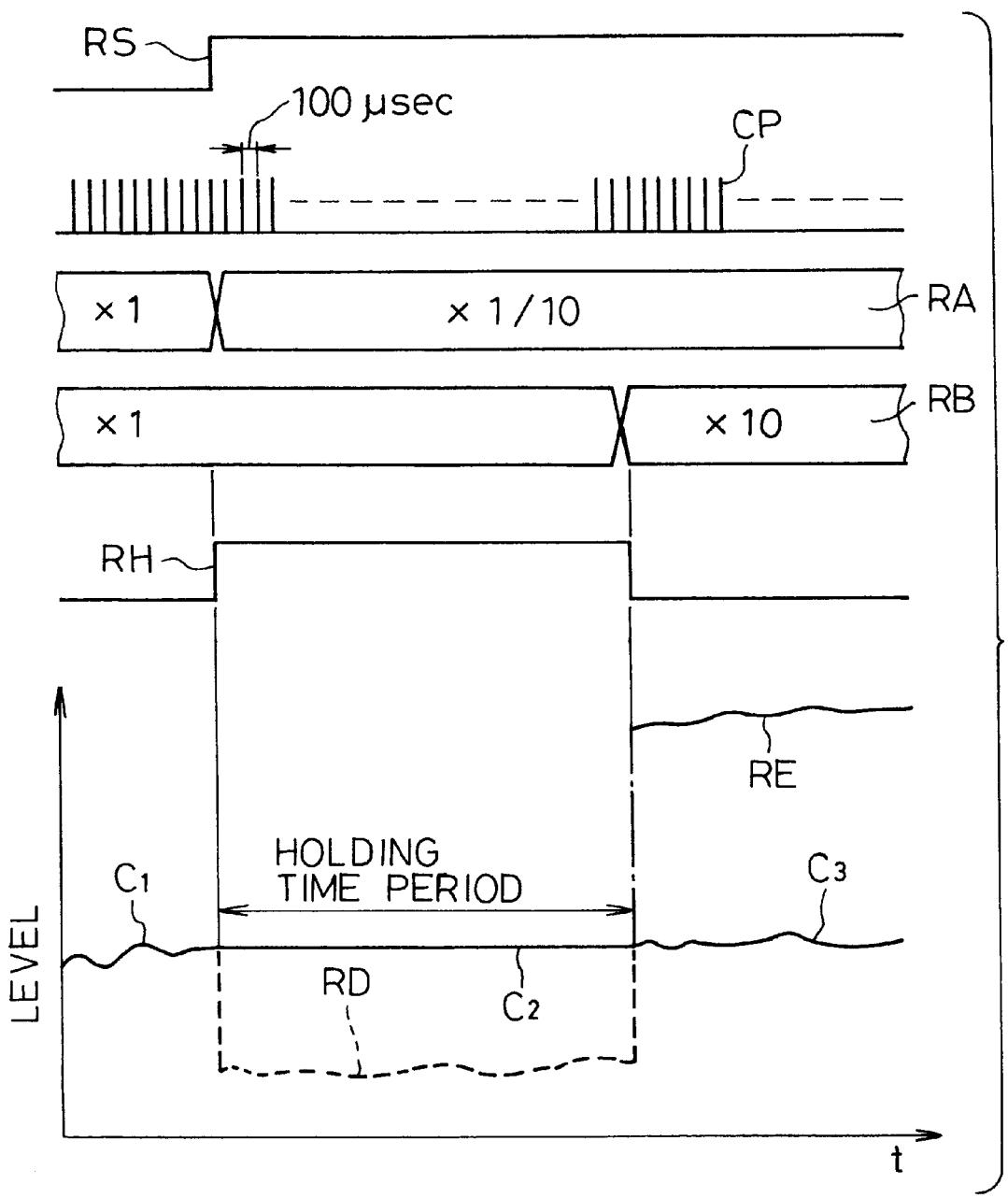
FIG. 4 is a timing chart showing operations of a digital coefficient unit and a hold circuit shown in FIG. 3.

During the control action of the control system constructed as mentioned above, if the range-selection instructing signal RS to instruct the switching of amplification factor, e.g., from ×1 to ×10 is given to the range-selection controlling section 212, as shown in FIG. 4, the coefficient unit 214 operates, under the control of the controlling section 212, to rapidly change the coefficient, e.g., from a value of 1 to a value of 0.1 in synchronism with clock CP which specifies the control cycle, until when the next clock is generated, as shown by symbol RA in FIG. 4. Contrary to this, the range selection in the detection amplifier 8a to change the amplification factor, e.g., from ×1 to ×10 is completed with a delay of several tens of milliseconds with respect to the range-selection instructing signal RS, as shown by symbol RB in FIG. 4.

The range-selection controlling section 212 outputs a hold signal, as shown by symbol RH in FIG. 4, at a timing determined by taking account of the time period required for the detection amplifier 8a to carry out the range selection, thereby causing the hold circuit 215 to operate. As a result, until the range selection in the detection amplifier 8a is completed, the digital detection value C1 just before the range selection is held in the hold circuit 215, so that the error unit 8b is supplied with a constant digital detection value C2. More specifically, the hold circuit 215 operates to hold the output of the digital coefficient unit 214 observed just before the coefficient value in the unit 214 is switched and supplies the same to the error unit 8b. After completion of the range selection in the detection amplifier 8a, a detection value C3 determined under a new detection range is supplied to the error unit 8b.

In the meantime, until the range selection in the detection amplifier 8a is completed, the digital coefficient unit 214 subjects the output of the AD converter 213 to the coefficient processing, assuming that the range selection is already finished. As a consequence, the output of the digital coefficient unit 214 largely differs from the original level of the detection value, as shown by symbol RD in FIG. 4. If the amplification factor in the detection amplifier 8a is set to a value of ×10, the digital coefficient unit 214 carries out the coefficient processing to reduce the output of the AD converter 213 by a factor of 10, in an attempt to keep the detection scale factor at a constant. Actually, however, the amplification factor in the detection amplifier 8a is not switched to ×10 as yet, and the detection value subjected to the coefficient processing is at the level which is one-tenth of the intended level of the detection value, as shown by symbol RD in FIG. 4. In order to prevent the signal RD which greatly differs in detection level from the intended level from being supplied to the error unit 8b, the range-selection controlling section 212 causes the hold circuit 215 to operate. By holding the detection value supplied from the digital coefficient unit 214 just before the range selection, the digital coefficient unit 214 is prevented from outputting an undesired detection value to the error unit 8b.

After completion of the range selection in the detection amplifier 8a, the detection value supplied from the detection amplifier 8a corresponds to the amplification factor, as shown by symbol RE in FIG. 4. At this stage, the digital coefficient unit 214 subjects the detection value RE to the coefficient processing in which the coefficient value of 0.1 suited to the new amplification factor, i.e., ×10, in the detection amplifier 8a is used. On and after extinction of the hold signal RH, the hold circuit 215 permits the detection value C3 obtained by the coefficient processing in the digital coefficient unit 214 to pass therethrough, so that the detection value C3 is supplied to the error unit 8b.

According to the testing machine of this embodiment which has the function of holding the detection value just before the range selection is instructed until the range selection in the detection is completed, to thereby hold the level of the control output value supplied to the servo system 11 at constant, the continuity of the detection value supplied, e.g., to the error unit 8b can be maintained even if the range or amplification factor in the detection amplifier 8a is switched as required in dependence on testing state during the material testing while operating the servo system 11. This makes it possible to detect the controlled variable, i.e., the force applied to the test piece or the displacement generated in the test piece, in a detection range which provides the amplification factor suited to the controlled variable or the control target value, with adequate SN ratio, whereby a stable feedback control can be made with high accuracy.

With the aforementioned arrangement, the coefficient suited to the amplification factor or detection range in the detection amplifier 8a is set in the digital coefficient unit 214, so that the scale factor in detecting the detection value supplied to the error unit 8b is kept at constant. Thus, it is unnecessary to adjust the level of the control target value supplied from the signal generator 8d to the error unit 8d. Since the gain in the signal detection system is maintained at constant, it is unnecessary to adjust the control gain in the digital controller 8c. As a consequence, the detection range (amplification factor) in the detection system can be switched with ease.

Furthermore, since the detection range in the detection system can be switched as needed while controlling the operation of the servo system 11, it is possible to avoid an unstable operation of the control system during the range selection. This makes it possible to carry out the switching of detection range in an adaptive manner in accordance with the material testing state, whereby the testing machine can be easily handled and the testing efficiency can be improved.

A second feature of the material testing machine according to the present embodiment resides in that the control section 8 of the testing machine is configured, during the mounting of the test piece S to the machine body, by the displacement control system which feedback-controls the operation of the servo system 11 in accordance with the displacement of the actuator 3 (test piece S), and in that it comprises correction means for correcting the target displacement, given to the displacement control system, in accordance with the force applied to the test piece S from the actuator 3 under the control of the displacement control system. Meanwhile, the testing machine is adapted to be mounted with a test piece S between the load cell 1 and the die 3a coupled to the movable rod 3b of the actuator 3.

Figure 5:
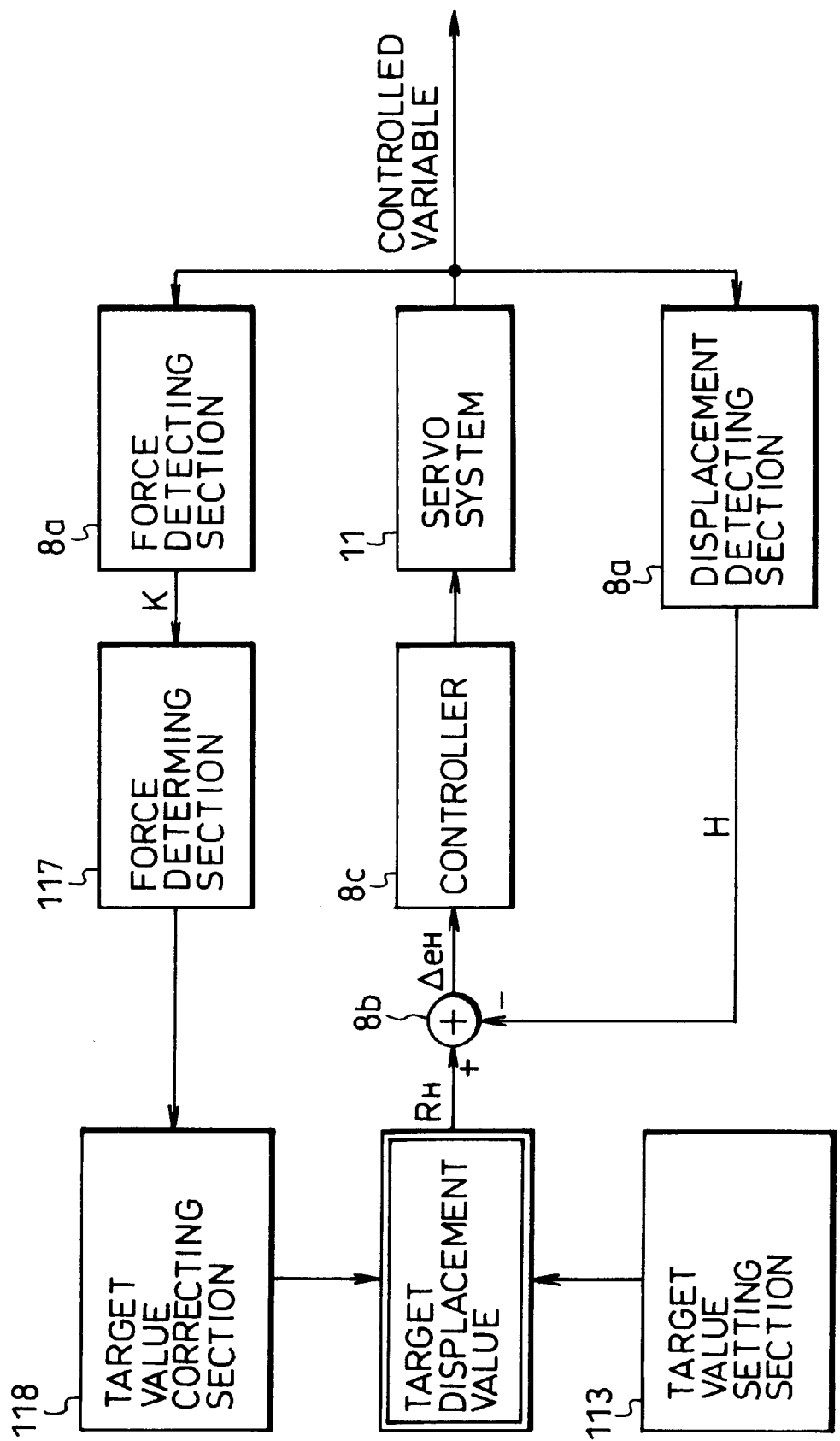
FIG. 5 is a block diagram showing an automatic test piece mounting function of the control system of the material testing machine.

As shown in FIG. 5, the displacement control system of the testing machine comprises displacement detecting means (detection amplifier 8a) for detecting, from the output of the displacement gauge 6, the actual displacement (controlled variable) of the actuator 3 which indicates the quantity of operation of the servo system 11; an error unit 8b for determining the error $\Delta e_H$ between the actual displacement H and the target displacement $R_H$ manually set by the operator through target value setting means 13 which is comprised of a key manipulating section (not shown) and the like; and a controller 8c for feedback-controlling the operation of the servo system 11 so as to reduce the error $\Delta e_H$ to zero.

The correction means of the machine is comprised of force detecting means (detection amplifier 8a) for always detecting, from the output of the load cell 1, the force K applied from the actuator 3 to the test piece S; force determination means 117 for determining the magnitude of the detected force; and target value correcting means 118 for correcting the target displacement $R_H$ in accordance with the determined force. The correction of the target displacement based on the detected force is always carried out at intervals of control cycle, irrespective of whether or not the displacement control for the actuator 3 by means of the displacement control system is stabilized, in other words, irrespective of whether or not the actuator 3 is displaced up to the displaced position indicated by the target displacement.

Figure 6:
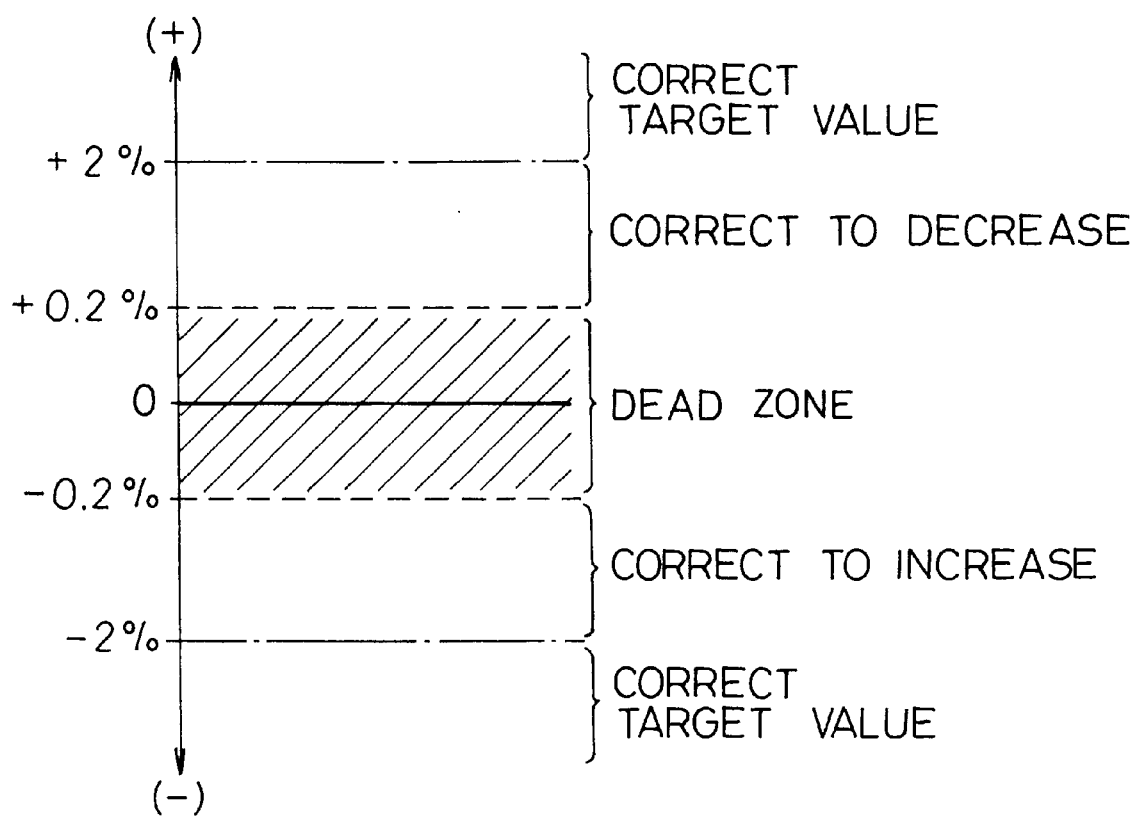
FIG. 6 is a view showing a relationship between the correction of target displacement and a force applied to the test piece during the automatic test piece mounting.

For instance, the force determination means 117 determines whether the force applied to the test piece S and detected by the load cell 1 is such a large force equal to or greater than 0.2% of the full scale of detection of the load cell or such a small force less than 0.2% of the full scale of detection. As shown in FIG. 6, the force less than 0.2% of the full scale falls within a dead zone of the detection system which includes the load cell 1 and is hence regarded as being substantially zero.

The target value correcting means 118 corrects the target displacement $R_H$ based on the result of force determination, in such a manner that the load applied to the test piece S by the actuator 3 of the servo system 11 controlled by the displacement control system becomes zero, i.e., the force K applied to the test piece S becomes less than 0.2% of the full scale of detection.

If the detected force K exceeds 0.2% of the full scale, the force K detected at that time is multiplied by a predetermined constant $\alpha$, for instance, to effect equivalent transformation of the force component into the equivalent component in the displacement control system, thereby obtaining the converted value (voltage value) $\alpha \cdot K$ as a correction value. This correction value $\alpha \cdot K$ is subtracted from the controlled variable (voltage value equivalent to displacement) H which is fed back to the displacement control system at that time point, and the resultant value is set as new target value $R_H$, thereby correcting the target displacement $R_H$. The constant $\alpha$ corresponds to the ratio between the control gain of the force control system and that of the displacement control system, and is determined in advance in accordance with the elastic constant of the test piece S or the like.

According to the arrangement where the target displacement supplied to the displacement control system is corrected in accordance with the force applied to the test piece S during the mounting of the test piece S on the testing machine body, so as to reduce the force applied to the test piece S to zero, i.e., to reduce the applied force below 0.2% of the full scale of detection of the load cell 1, the displacement of the actuator 3 of the servo system 11 can be controlled appropriately, whereby the force applied to the test piece S during the mounting the test piece to the machine body can be reduced to zero. In particular, the operation of the servo system 11 is controlled to specify the displacement position of the actuator 3 with high accuracy, while correcting the target displacement depending on the force applied to the test piece, without causing an abrupt change in the target displacement. This makes it possible to stably mount the test piece S on the machine body under non-load states, without applying an excessive load to the test piece S. Thus, the mounting work of the test piece S becomes easy and the mounting efficiency can be greatly improved.

Figure 7:
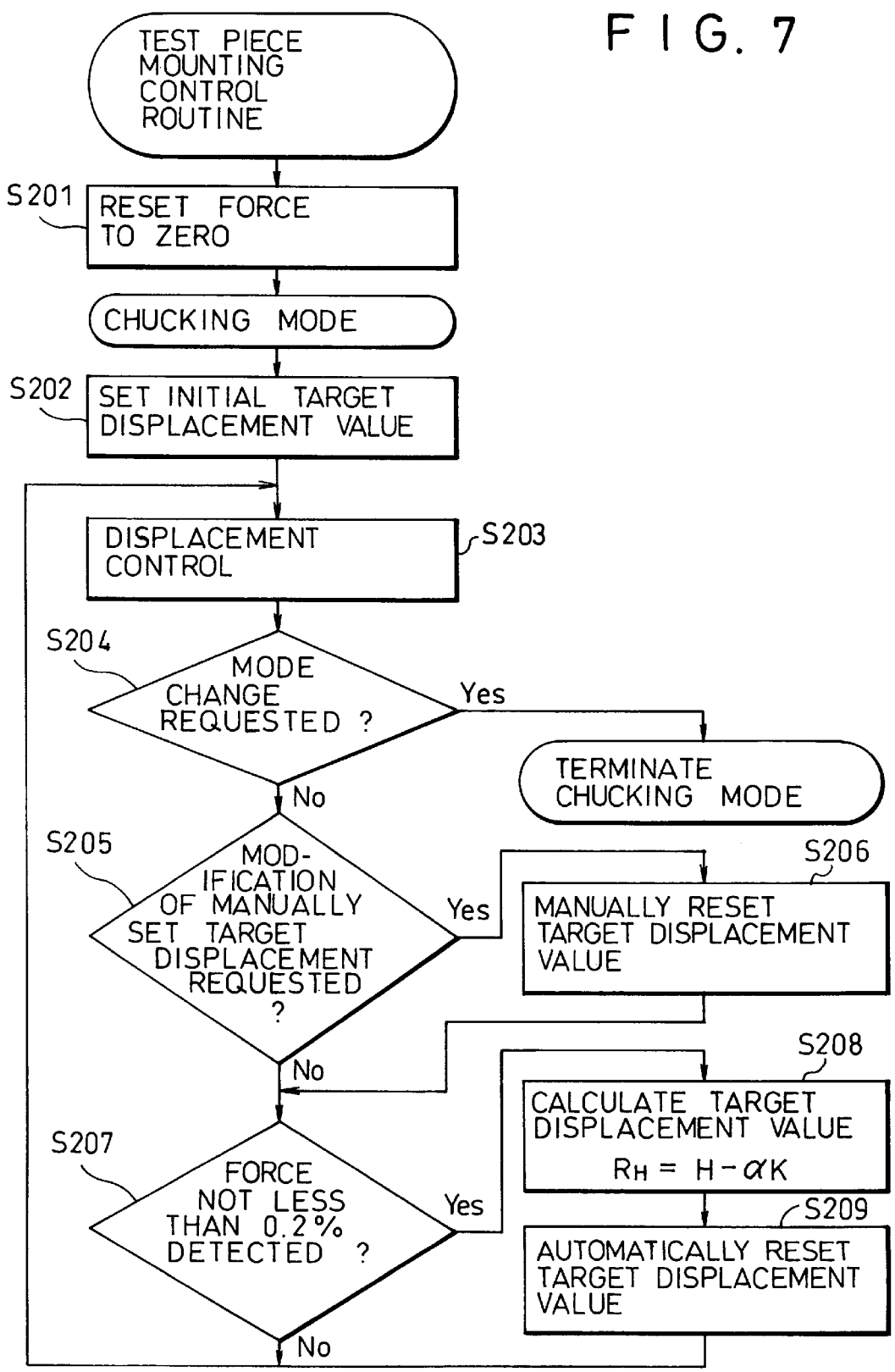
FIG. 7 is a flowchart of a test piece mounting routine.

FIG. 7 shows a test piece mounting control routine executed by the controller 8c during the mounting the test piece on the machine body.

The test piece mounting control routine is started after the movable rod 3b of the actuator 3 is initially set to a predetermined reference position and then the test piece S is placed on the die 3a (more generally, movable chuck) of the movable rod 3b of the actuator 3. Under this test piece placement condition, the test piece S is naturally in a state where it is located apart from the load cell 1 (more generally, the stationary chuck 2a). In this regard, the force detected by the load cell 1 is reset to zero (step S201), to thereby remove affections of external factors on the load cell 1. Then, the test piece chucking mode is started.

Subsequently, the initial setting of a target movement amount, serving as the target displacement $R_H$, of the actuator 3 is automatically carried out based on control program or manually by the operator through the key manipulation section 113 (step S202). Whereupon, the displacement control system is actuated, whereby the servo system 11 is feedback-controlled using the actual displacement of the actuator 3 as the controlled variable, so as to cause the actuator 3 to be displaced to the target moving position (step S203).

During the displacement control, a request for mode change is monitored (step S204). If the mode change is requested, the chucking mode is terminated and is changed over to a requested operation mode.

If it is determined at step S204 that no request for mode change is made, the chucking mode is continued, and a request for modification of manual setting in respect of the target displacement $R_H$ is determined (step S205). If the modification request is made for the reason that the initial value of the target displacement set at step S202 is excessively small or large or the like, the control flow awaits for manual input of the target displacement $R_H$ by the operator, and modifies the target displacement $R_H$ to a manually input new target displacement (step S206). Subsequently, the chucking mode is executed with use of the new target displacement $R_H$.

During the chucking mode, whether or not a force is applied to the test piece S from the movable rod 3b of the actuator 3 is determined at intervals of a period (e.g., period of 100 μsec) determined depending on the control cycle of the controller 8c (step S207). If the applied force is not detected, the control flow returns to step S203. On the other hand, if the force applied to the test piece S is detected, especially if the force which exceeds 0.2% of the full scale of the load cell 1 is detected, in order to the force to reduce to zero, the product of the load K detected at that time and a conversion coefficient α is subtracted from the actual displacement H of the movable rod 3b (test piece S) to thereby determine a new target displacement $R_H$ (step S208). Then, the new target displacement $R_H$ is set. By doing this, the target displacement $R_H$ is corrected in accordance with the detected force K (step S209). As a result, the force applied to the test piece S is caused to be zero, i.e., is caused to reduce to a value falling within a range of 0.2% of the full scale of detection of the load cell 1.

Next, the control flow returns to step S203 where the displacement control is carried out. If the correction of the target displacement $R_H$ is made once at step S209, the displacement of the movable rod 3b of the actuator is rendered substantially zero, so that a non-load state where the force applied to the test piece S is kept substantially at zero is maintained. In this manner, the mounting of the test piece to the machine body is completed. It is convenient for the operator if he or she is informed of completion of test piece mounting when the correction of target displacement at step S209 is completed or when a predetermined time period has elapsed from the time point at which the correction was completed.

As explained above, the test piece mounting in this embodiment can be carried out by operating the displacement control system with use of the control algorithm which is relatively simple. In particular, the displacement position of the movable rod 3b of the actuator 3 is specified with high accuracy to reduce the load applied to the test piece to zero, by correcting the target displacement given to the displacement control system in accordance with the force applied to the test piece. Thus, the test piece S can be mounted to the machine body stably and securely under non-load states.

The present invention is not limited to the foregoing embodiment but may be modified variously.

For example, in order to prevent an unstable operation of the servo system 11 as the range selection is carried out in the detection amplifier 8a, the control output from the digital controller 8c to the servo system 11 may be held. Alternatively, the output (error value) of the error unit 8 may be held to prevent the unstable operation of the servo system. In this case, it is preferable to maintain the control target value supplied from the signal generator 8d to the error unit 8b as the detection range is being switched in the detection amplifier 8a.

Further, the correction amount α·K for the target displacement suited to the applied force K may be determined in dependence on the control gain of the displacement control system or the like. The correction calculating formula of H-α·K may be modified variously. Further, the scope of the dead zone in force detection may be determined in accordance with the specification of the testing machine or the load cell.

As for the initial setting of the movement position and target displacement of the movable rod 3b of the actuator 3, the manual setting is adopted in this embodiment in which a numerical value is input through the target value setting means 113 in a condition that the movable rod 3b is set at the reference position. Alternatively, the operator may perform button manipulations for repeatedly instructing stepwise increment/decrement of displacement, while visually watching the displacement of the movable rod 3b of the actuator 3, thereby carrying out the initial setting of movement position of the movable rod 3. In the initial setting of target displacement, a candidate for target displacement may be displayed on a display panel and may be increased and decreased stepwise in response to button manipulations, so that a desired target displacement may be manually set by pressing a final button when the candidate displayed in the display panel assumes a desired value.

It is understood that the present invention may be further modified without departing from the scope or spirit of the invention.

What is claimed is:

1. A material testing machine for measuring a mechanical property of a test piece based on a load given to the test piece and a mechanical change generated in the test piece, while feedback-controlling an operation of a servo system including a hydraulic actuator which gives the load to the test piece by means of a controller such that an actual load applied to the test piece coincides with a target load, said material testing machine including a detection amplifier operable at an amplification factor selected from a plurality of amplification factors, said detection amplifier operating to input an input signal indicative of a load applied to the test piece or a mechanical change generated in the test piece, amplify the input signal at a selected amplification factor to obtain an analog detection value, and output the analog detection value, said material testing machine including range selection means for switching the amplification factor selected in said detection amplifier, the improvement comprising:

detection scale-factor invariant means for processing a digital detection value, converted from the analog detection value supplied from said detection amplifier, in dependence on an amplification factor inversely proportional to the amplification factor selected in said detection amplifier, to thereby cause a detection scale factor in detecting a controlled variable in the feedback control to be invariant;

a signal generator for outputting a digital target value indicative of the target load;

a deviation unit for inputting the digital target value and the processed digital detection and for outputting a deviation signal indicative of a deviation therebetween; and control output holding means for holding a control output value at a value observed just before the amplification factor is switched, while the amplification factor of said detection amplifier is being switched, the control output value being supplied to the servo system from a digital controller which performs a feedback-control action in accordance with the deviation signal.

2. The material testing machine according to claim 1, wherein said detection scale-factor invariant means includes an analog-to-digital converter for converting the analog output value supplied from said detection amplifier into the digital detection value, and a digital coefficient unit for performing coefficient processing in which the digital detection value supplied from said analog-to-digital converter is multiplied by a coefficient value inversely proportional to the amplification factor selected in the detection amplifier such that the detection scale factor is rendered invariant.

3. The material testing machine according to claim 1, wherein said control output holding means is comprised of a hold circuit for holding an output value supplied from said digital coefficient unit just before the amplification factor of said detection amplifier is switched, until the switching of the amplification factor is completed.

4. A material testing machine for measuring a mechanical property of a test piece based on a load given to the test piece and a mechanical change generated in the test piece, while feedback-controlling an operation of a servo system including a hydraulic actuator which gives the load to the test piece by means of a controller, such that an actual load applied to the test piece coincides with a target load, said material testing machine including a machine body having a test piece mount which is coupled to a movable part of the actuator; a displacement control system including a controller for feedback-controlling the operation of the servo system so as to cause an actual displacement of the movable part of the actuator to coincide with a target displacement; and a force detector for detecting an actual force applied to the test piece as the movable part of the actuator is displaced; the improvement comprising:

correction means for correcting the target displacement of the movable part of the actuator in accordance with the actual force applied to the test piece such that the actual force does not exceed a predetermined force determined depending on a detection resolution of the force detector, as the test piece is mounted to the machine body while executing the feedback control by the displacement control system.

5. The material testing machine according to claim 4, wherein said correction means corrects the target displacement so as to decrease when the actual force, applied to the test piece and detected by the force detector, exceeds a detection resolution of the force detector.

* * * * *